(12) United States Patent
Oz

(10) Patent No.: US 9,254,080 B2
(45) Date of Patent: Feb. 9, 2016

(54) METHOD AND SYSTEM FOR TREATMENT OF VISUAL IMPAIRMENT

(75) Inventor: Dan Oz, Even Yehuda (IL)

(73) Assignee: Improved Vision Systems (I.V.S.) Ltd. (IL)

(*) Notice: Subject to any disclaimer, the term of this patent is extended or adjusted under 35 U.S.C. 154(b) by 0 days.

(21) Appl. No.: 14/342,665

(22) PCT Filed: Jun. 21, 2012

(86) PCT No.: PCT/IL2012/000305
§ 371 (c)(1),
(2), (4) Date: Mar. 4, 2014

(87) PCT Pub. No.: WO2013/035086
PCT Pub. Date: Mar. 14, 2013

(65) Prior Publication Data
US 2014/0300859 A1 Oct. 9, 2014

Related U.S. Application Data

(60) Provisional application No. 61/531,630, filed on Sep. 7, 2011.

(51) Int. Cl.
*A61B 3/08* (2006.01)
*A61B 3/00* (2006.01)
*A61B 3/14* (2006.01)
*G02B 27/22* (2006.01)
*G02B 27/01* (2006.01)
*A61B 3/113* (2006.01)
*G06K 9/00* (2006.01)

(52) U.S. Cl.
CPC .............. *A61B 3/0025* (2013.01); *A61B 3/113* (2013.01); *G02B 27/017* (2013.01); *G02B 27/225* (2013.01); *G06K 9/00604* (2013.01); *G02B 2027/0138* (2013.01); *G02B 2027/0178* (2013.01); *G02B 2027/0187* (2013.01)

(58) Field of Classification Search
USPC .................................................. 351/200–246
See application file for complete search history.

(56) References Cited

U.S. PATENT DOCUMENTS 5,592,247 A * 1/1997 Trokel ........................... 351/239
5,875,018 A * 2/1999 Lamprecht .................... 351/208
5,892,570 A    4/1999 Stevens (Continued)

FOREIGN PATENT DOCUMENTS

GB     1096997 A    12/1967

OTHER PUBLICATIONS

"1280 X 1024 Low Power Color Amoled Microdisplay," SXGA, eMagin Corporation, Revision 6, Sep. 2010, pp. 1-68.
"SMI Eye Tracking Glasses 2.0: Objective Insights into Real-World Visual Behavior," SMI SensoMotoric Instruments, Sep. 2013, 4 pages.
"DogCam Bullet HD Wide," PRofessional Helmet Camera Systems, 2006, 1 page, September.

(Continued)

*Primary Examiner* — Mohammed Hasan
(74) *Attorney, Agent, or Firm* — Blank Rome LLP

(57) ABSTRACT

Method and system for treating of visual impairment associated with misalignment between eyes of a patient is described. The invention allows to obtain electronically of an image of an object at which one eye of the patient is staring, calculating angular deviation between staring direction of this eye and the second eye and displaying before the second eye the image after it has been electronically processed so as to correct the angular deviation and to obtain the image, which would be perceptible by the brain as a single three dimensional stereoscopic image.

15 Claims, 10 Drawing Sheets

(56) References Cited

U.S. PATENT DOCUMENTS

| | | | |
|---|---|---|---|
| 6,099,124 | A | 8/2000 | Hidaji |
| 7,206,022 | B2 | 4/2007 | Miller et al. |
| 7,232,219 | B2 * | 6/2007 | Aguilar et al. ........... 351/159.58 |
| 7,859,562 | B2 | 12/2010 | Igarashi et al. |
| 2010/0177179 | A1 | 7/2010 | Behm et al. |
| 2011/0050546 | A1 | 3/2011 | Swartz, Jr. et al. |

OTHER PUBLICATIONS

"1280 X 1024 Low Power Color Amoled Microdisplay," SXGA, eMagin Corporation, Revision 10, Jul. 2013, pp. 1-71.

International Search Report issued on Dec. 9, 2012, in International Patent Application No. PCT/IL2012/000305, 3 pages.

Statement Under PCT Article 19 filed on Jan. 29, 2013, in International Patent Application No. PCT/IL2012/000305, 2 pages.

\* cited by examiner

METHOD AND SYSTEM FOR TREATMENT OF VISUAL IMPAIRMENT

FIELD OF THE INVENTION

The present invention relates to ophthalmology and more specifically to treatment of visual impairment caused by a condition in which eyes of a patient are not properly aligned such that the gaze of each eye is not directed to the same point in space, thus preventing proper binocular vision.

More particularly the present invention concerns a method and a system for treatment of visual impairment associated with pathologies of the extra ocular eye muscles or with other problems causing a phenomenon known as diplopia (Double Vision). One of pathologies causing diplopia is known as strabismus. It should be borne in mind however, that the present invention is not limited merely to treatment of strabismus and it can be used also for treatment of other kinds of visual impairment associated with diplopia. One should also bear in mind that the present invention can be used not merely for therapeutic treatment per se but also for training and/or rehabilitation of people suffering from visual impairment.

BACKGROUND OF THE INVENTION

Normal human has horizontal vision field of view (FOV) when his/her head and eyes are fixed is about 160° with one eye and is approximately 190° with two eyes. This is schematically depicted in FIG. 1. The vertical FOV is about 50° up and 80° down.

In FIG. 2 is shown binocular horizontal region seen by both eyes simultaneously. This region is confined by an angle of about 130° and it is responsible for depth perception.

The normal way the human eyes stare at an object is rather complicated. The eye movements are governed by six extra ocular eye muscles. The eye various movements must be performed by both eyes in a coordinated manner to ensure proper fixation and depth perception. The main movements are:

Saccadic movement & Smooth pursuit
Microsaccades
Vergence movement
Below those movements are explained in more details.

Saccadic movements allow a person to look at the desired object. The staring is composed of both eye movements and eyes rotation into the proper gaze direction.

As seen in FIG. 3 the head-fixed horizontal saccades can have amplitudes of up to a total of 130° (75° temporal direction and 55° nasal direction) but in normal conditions the saccades are far smaller, and any shift of gaze direction larger than about 20° is accompanied by a head movement. During such gaze saccades, first the eye produces a saccade to get gaze on a target, whereas the head follows more slowly and the eyes roll back to keep gaze on the target.

For saccadic amplitudes of up to about 60°, the velocity of a saccade linearly depends on the amplitude (the so called "saccadic main sequence"). For instance, 10° amplitude is associated with a velocity of 300°/sec, and 30° amplitude is associated with 500°/sec. In saccades larger than 60°, the peak velocity starts to plateau (nonlinearly) toward the maximum velocity attainable by the eye.

Smooth pursuit eye movements allow the eyes to closely follow after a moving object.

Micro saccades are a kind of fixation, tiny and rapid eye movements having usually amplitudes of up to 2°. They are small, jerk-like, involuntary eye movements, similar to miniature versions of voluntary saccades. The role of micro saccades in visual perception has been a highly debated topic which is still largely unresolved.

A vergence is the simultaneous movement of both eyes in opposite directions to obtain and maintain single binocular vision. When a person looks at an object, the eyes must rotate around a vertical axis so that the projection of the image is in the centre of the retina in both eyes. To look at an close object, the eyes rotate towards each other (convergence), while for looking at a distant object they rotate away from each other (divergence).

An example of the angle δ by which the eyes have to rotate "in" for a near distance to the object e.g. of 350 mm is shown in FIG. 4. This angle δ is calculated as Arctg δ=IPD/2×D, where IPD is interpupillary distance and D is distance to the object. In the situation depicted in FIG. 4 the IPD is assumed 65 mm and D=350 mm.

Thus one can readily appreciate that extra ocular muscles should be able to displace the eyes in a very complex and at the same time coordinated manner in order to ensure normal visual perception. It can be readily appreciated that any disturbance in movement of at least one eye would be associated with misalignment resulting in visual impairment.

In a further disclosure the following terms will be used:

The term "leading eye" refers to a normal, healthy eye. In case of alternating strabismus, the leading eye will be determined by the processing unit.

The term "non-leading eye" or "tilted eye" refers to an eye that has a problem—for example, partial or full immobility resulting in that it is not staring at the desired direction and cannot be displaced in a coordinated manner with the leading eye.

The term "wide-angle camera" refers to a video camera with a relatively short focal length that permits an angle of view wider than approximately 70°.

The term "digital camera" refers to a video camera that is equipped with a solid state sensor (CCD or CMOS or other sensor) that enables capturing and providing the captured images in digital form.

The term "eye tracking" refers to the process of measuring either the point of gaze ("where we are looking") or to the motion of an eye relative to the head.

The term "eye tracker" refers to a device for measuring eye positions and eye movement.

The terms "gaze", "stare" and their conjugates could be used alternately and mean "to look at an object of a scene"

The Problem to be Solved

Many people of all ages suffer from variable pathologies of the extra ocular eye muscles or the oculomotor nerve or the brain. Such pathologies may result in the so-called strabismus, i.e. a condition in which one eye is not able to stare at the same direction in space as the other eye and hence there exists misalignment between both eyes. Due to this misalignment double vision (Diplopia) may occur.

The ocular misalignment can be horizontal, and/or vertical, and/or torsional.

In some kinds of strabismus, the non-leading eye has a constant angular deviation from the desired direction (this is known as esotropia or exotropia); it can be staring at a fixed direction in space, move freely around etc. All these phenomena can be associated both with horizontal and/or torsional and/or vertical field of view.

Nonparalytic strabismus, with all its derivatives, is a kind of visual impairment in which despite the extra ocular muscles operate, nevertheless, the muscles do not turn the non-leading eye to track exactly the required direction dictated by the leading, healthy eye. Exotropia, esotropia, hypertropia, heterophoria etc. are but a few examples for nonparalytic strabismus.

Paralytic strabismus, with all its derivatives, is a kind of visual impairment in which some or all the extra ocular muscles are partially or fully non operative, resulting in partial or full paralysis of the non-leading eye.

In a more severe situation, all those problems can occur in both eyes.

The above mentioned pathologies are caused by various reasons. Among possible reasons could be mentioned brain disorder in coordinating the eye's movement, problems associated with the oculomotor nerve or problems associated with one or more of the extra ocular muscles.

In an attempt to avoid double vision, the brain may sometimes ignore the image from one eye, a process known as suppression or amblyopia. The suppressing is more frequent in childhood when the brain is still developing. Thus, the children with strabismus almost never complain of diplopia while adults who develop strabismus almost always do. In the developing child this can prevent the proper development of vision in the affected eye resulting in amblyopia. Some adults are also able to suppress their diplopia, but their suppression is rarely as deep or as effective and takes longer to establish. Thus, many of those people having double vision suffer from blurred vision, eyes pain, headache, nausea, balance problems and more. If not treated otherwise, the non-leading eye has to be covered, suppressed or degenerated. This is associated with deterioration of depth perception.

One should appreciate however that the pathologies which are mentioned above should be considered as merely non-limited examples of visual impairment which can be treated by the present invention.

There are known attempts to resolve problems associated with visual impairment due to misalignment between the eyes and in particular with the impairment associated with strabismus.

In GB 1096997 is disclosed apparatus for treating strabismus. This apparatus is intended for correcting strabismus and it comprises a screen, a cinematograph for producing two complementary images on the screen and two ophthalmoscopic arrangements so disposed that they transmit different ones of the images to different eyes of the patient and allow examination of the images formed on the retina of each eye, the arrangements being independently adjustable for alignment with the respective optical axes of the patients' eyes. The arrangement of the apparatus is such that the composite image viewed by the patient appears to be on the screen and the screen may be touched by the patient to re-educate the eyes.

The most close to the present invention is a method and device proposed by J. Lamprecht in his U.S. Pat. No. 5,875, 018 filed on Sep. 26, 1994.

The invention described in this patent is based on the idea to use a mechanically swiveled video camera for producing an image that should be seen by the non-leading eye if it would be normal and displaying this image via a bundle of fiber optics on a screen located before non-leading eye. Before the produced image is displayed it is brought into angular correspondence with the image seen by the leading eye taking into account the angular deviation between the leading and the non-leading eye.

To establish angular correspondence, the staring angle of the leading eye should be determined by eye tracker, then the video camera producing the image for the non-leading eye is mechanically swiveled so as to be directed at the staring angle and the image produced by the camera is projected on a screen located opposite to the non-leading eye.

This idea however was never implemented as a real commercially available apparatus suitable for persons suffering from various kinds of strabismus.

Some of the reasons which probably prevented practical realization of the Lamprecht's idea are listed herein:

a. Mechanically swiveled video camera which should track the staring angle of the leading eye requires time for changing direction of view of the camera. Since eye movements are very rapid, the image produced by mechanically swiveled camera will lag behind the fast movement of the leading eye and therefore instead of real image a non realistic transient image would be produced by the camera and the real image seen by the leading eye and the lagging image produced by the mechanically driven camera would not be able to be integrated by the brain.

b. Mechanically swiveled video camera is cumbersome and heavy: it is complicated, expensive and needs maintenance.

c. Mechanical systems in general and mechanically swiveled cameras in particular require higher energy for their operation and thus heavier batteries.

d. The image producing device employed in the apparatus of Lamprecht is connected to the viewing screen by fiber optics and the image is relayed to the viewing screen via a light conducting fibers bundle. This solution is cumbersome and does not allow to achieve high resolution image since the number of light conducting strands (fiber optics) in the bundle is limited. The required number of pixels for a good quality image is in the range of millions; however fiber optics bundle consisting of millions strands would be impractical.

Due to the mentioned above reasons the Lamprecht's solution resulted in a big, heavy and cumbersome apparatus, designed as a helmet. Nevertheless, even though such helmet apparatus could be feasible, it would be not practical for everyday use and will not allow sufficient resolution for obtaining good quality image since a resolution provided by light conducting cable is limited.

In conclusion one could state that even though the Lamprecht's idea has been devised as early as in 1994, the long felt problem of impaired vision associated with the eyes misalignment still remains unsolved and requires proper solution.

OBJECTS AND A BRIEF SUMMARY OF THE PRESENT INVENTION

The main object of the present invention is to provide an improved method and system for treatment of visual impairment enabling to sufficiently reduce or to overcome the drawbacks of the known in the art solutions.

In particular the first object of the invention is to provide a new and improved method and system for treatment of visual impairment employing a wide angle digital camera, which is substantially still and which does not require mechanical displacement, e.g., swiveling for tracking of viewing angle of an eye.

Still further object of the invention is to provide a new and improved method and system for treatment of visual impairment employing a wide angle miniature CCD or CMOS video camera located in proximity to the non-leading eye and there is no need in a light conducting cable for electrical connecting between processing unit and display.

Still further object of the invention is to provide a new and improved method and system for treatment of visual impairment employing a processing unit.

The other object of the invention is to provide a new and improved method and system for treatment of visual impairment which can be implemented as a compact, light and convenient eyewear.

Another object of the invention is to provide a new and improved method and system for treatment of visual impairment which enables reliable eye tracking with a speed corresponding to the speed of eye movements.

Yet another object of the invention is to provide a new and improved method and system for treatment of visual impairment which enables producing a good quality image with required resolution and displaying this image without distortion before a non-leading eye.

The above mentioned objects are achieved by the present invention when it is implemented as a method of treatment and a system for treatment of visual impairment. In particular when the invention is implemented as a method it comprises the following features:
  selecting one eye as a leading eye while selecting a second eye as a non-leading eye,
  tracking a current position of the leading eye when it is staring at a scene and determining a current staring direction of the leading eye
  obtaining electronically of an image of the scene stared at by the patient, said image is confined within a view angle of at least 70 degrees,
  tracking a current position of the non-leading eye and determining a staring direction of the non-leading eye,
  calculating an angular deviation between the staring direction of the leading eye and the staring direction of the non-leading eye,
  electronically processing the image of the scene such that after processing the image would be electronically shifted, in accordance with the angular deviation and displaying the shifted image in front of the non-leading eye.

When the present invention is implemented as a system, it is dimensioned and configured as an eyewear with affixed thereto a tracking device capable of tracking movements of at least one of the patient's eyes, an image producing device capable of electronically producing an image of a scene appearing in front of the patient, a processing unit capable to electronically process the image along with a tracking data produced by the tracking device, a display device capable of visually displaying the electronically processed image in front of the at least one of the patient's eyes and said eyewear is electrically connected with a source of energy for energizing the tracking device, the image producing device, the processing unit and the display device.

The main idea lying behind the present invention is to employ a miniature, wide angle digital video camera which can be still and don't require mechanical displacement for obtaining the whole image of a scene seen by the leading eye. The camera will be electronically producing virtual image of the scene and then delivering this image after it has been electronically processed to the non-leading eye. Such a camera is capable to electronically scan the entire required field of view. The scanning can be done reliably and with a speed corresponding to velocities of the eye movements. Since the camera is miniature the whole system can be implemented for example as a compact eyewear conveniently worn by a patient.

By virtue of the processing unit it would be possible to monitor automatically the results of treatment and to change parameters of the treatment if required.

It should be emphasized that digital video cameras have been known for a relatively long period and in particular they were available at the time of filing the Lamprecht's patent application. Nevertheless, digital video camera was neither employed then nor is it used now, despite the problem of impaired vision due to the eye's misalignment, persists for a very long time. This fact indicates that the present invention is not obvious.

The other feature employed in the present invention is using of a miniature image producing device and placing the image producing device in close proximity to at least one of the eyes. By virtue of this provision the image sent to the display device may have high resolution since there is no need in a cumbersome bundle of fiber optics to relay the image.

The present invention will be suitable for patients suffering from visual impairment associated with at least partial diplopia of at least one eye.

The present invention could be used for training, vision therapy, rehabilitation, assessment, measurement, diagnosis and analysis of visual impairment.

In particular, the present invention could be used for treatment of patients suffering from various types of strabismus, like bilateral strabismus, unilateral strabismus, alternating strabismus, esotropic strabismus, exotropic strabismus and hypertropic strabismus In particular, the present invention would be suitable for treatment of visual impairments in the following three situations:
  1. Healthy leading eye, non-leading eye retains some moving capabilities
  2. Healthy leading eye, non-leading eye is fully paralyzed.
  3. Ocular misalignment of both eyes (both eyes have alternating strabismus, erratic or both eyes with conjugate gaze palsies).

The present invention has only been summarized briefly. For better understanding of the present invention as well of its embodiments and advantages, reference will now be made to the following description with reference to the accompanying drawings.

DETAILED DESCRIPTION OF THE INVENTION

Figure 5:
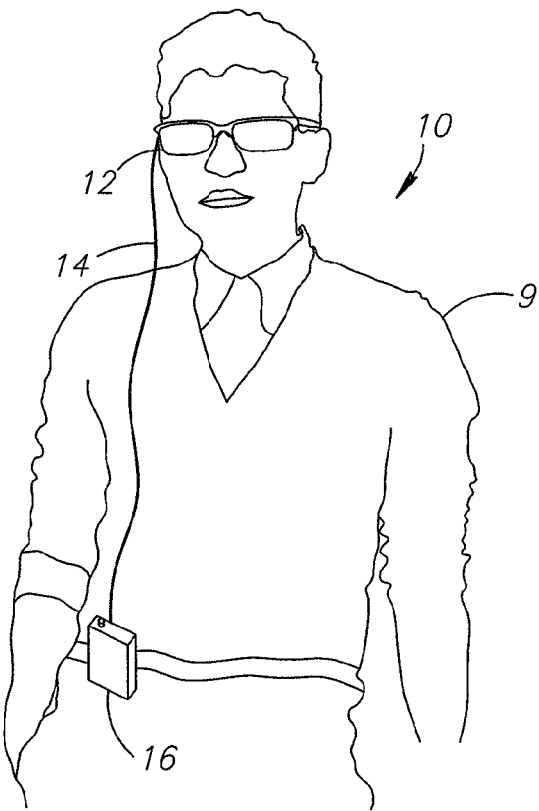
FIG. 5 depicts general view of the system of the invention when it is worn as eyewear by a patient.
Figure 6A:
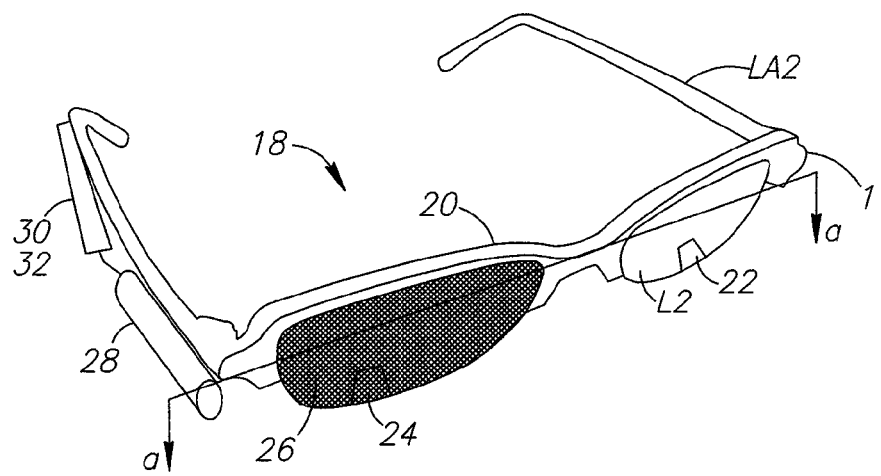
FIG. 6a shows an isometric view of an embodiment of the system of the present invention implemented as an eyewear.
Figure 6B:
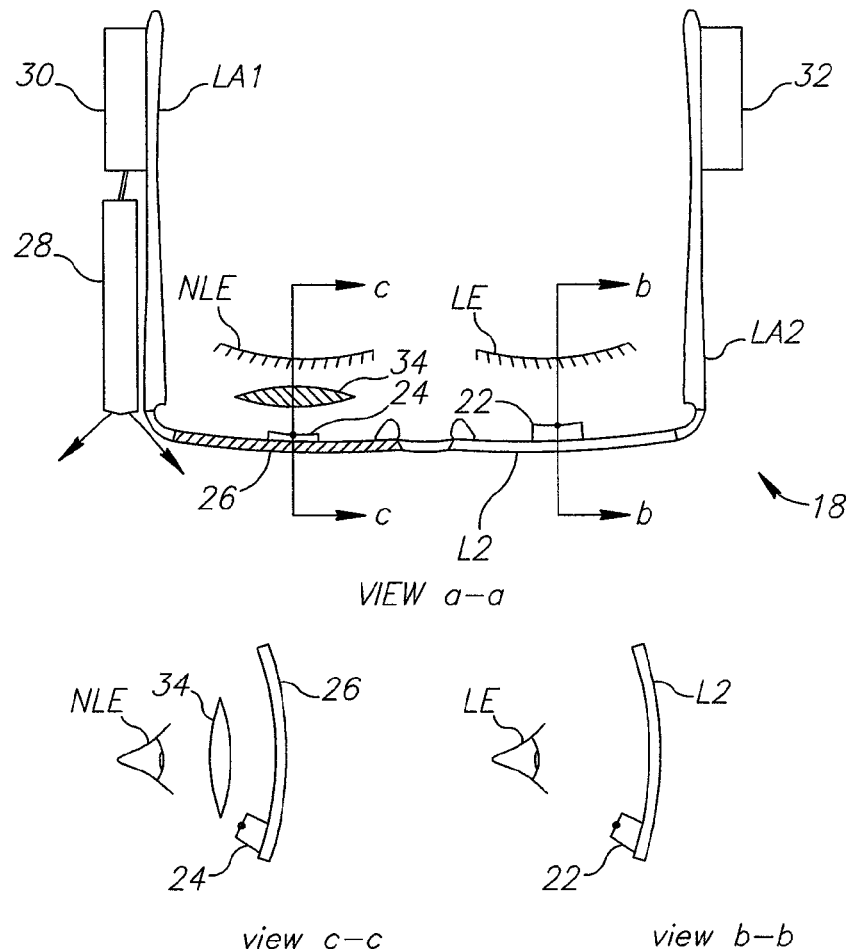
FIG. 6b shows schematically cross sections taken along a-a, b-b and c-c of the view presented in FIG. 5.
Figure 7:
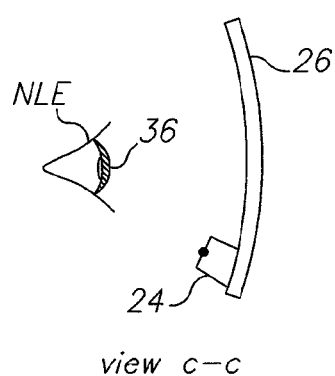
FIG. 7 shows schematically an alternative embodiment for the cross section c-c.

With reference to FIGS. 5-7 an embodiment of the system of the present invention is shown.

In general, a system 10 is seen, which comprises a wearable by a patient 9 a head unit 12 electrically connected via a connecting cable 14 to an external processing & energizing component 16. This component comprises a processing unit and a source of energy, e.g. battery pack.

In an alternative embodiment shown in FIG. 6a the system is configured as an integral head unit 18, comprising a processing unit & battery pack 30 being retrofitted within the head unit.

The head unit preferably is configured and dimensioned to be convenient in use when it is put on. This unit can be configured as eye glasses.

In the further disclosure it will be referred to as eyewear to include any of the related devices, such as spectacles, goggles, glasses etc. used for aiding the vision or for protecting the eyes.

In the further descriptions the term tracking of eyes will be mentioned mainly in connection with tracking of eyes by scanning in horizontal direction. It should be borne in mind, however, that the same applies to the vertical direction as well and the system of the invention is devised to be capable to measure, address and solve visual impairment problems associated with misalignment in torsional, horizontal and vertical gazing directions.

Referring to FIG. 6a the system of the present invention is designed as an eyewear configured for example as spectacles having a frame 20 with a lens L2. The lens L2 is transparent to provide unobstructed view for a leading eye. It may be a conventional lens or optical lens in the sense that it may have prescribed diopter number, providing that the patient has focusing problems.

The frame is provided with two lateral arms LA1 and LA2. Once the eyewear is put on the patient's head, lens L2 is opposite to the leading eye. A lens 34 is provided which is situated opposite to the non leading eye.

The eyewear carries a couple of eye trackers 22, 24, located in front and below the eyes. Exact position of each eye tracker is selected in such a manner that it is located about 2.5 cm below the corresponding eye and about 45 degrees below/forward. By virtue of this provision there is no obscuring. In practice the eye tracker can be a video camera based eye tracker have sampling rate of at least 30 Hz. An example of a suitable eye tracker is SMI GazeWear tracker manufactured by SensoMotoric Instruments GmbH, Germany.

The eyewear comprises at least one wide angle display device 26 overlapping with at least the non leading eye's field of view. In practice this display is located opposite to the non-leading eye. As suitable wide angle display device one can use micro display color screen EMA-100502 SXGA XL manufactured by eMagin Corporation, USA. This display has a total pixel array of 1292(×3)×1036 pixels.

The eyewear further comprises at least one wide angle, high resolution, miniature digital video camera 28, affixed to one of the lateral arms, preferably in vicinity to the non leading eye. This is required in order to achieve the correct parallax between the leading eye and the video camera for correct stereoscopic image. In practice the camera is situated aside of the non-leading eye and is separated therefrom by a distance of about 2.5 cm. The camera should have a view angle of at least 70 degrees preferably more than 100 degrees and it might be advantageous if the camera is provided with an auto focusing feature. The camera is secured on the frame such that is substantially still and within its field of view it scans the image of the scene electronically.

An example of a suitable camera is DogCam Bullet HD WIDE digital camera distributed by DCS Systems Ltd., England. This video camera is a 720p high definition video camera and it has a wide angle lens of 135 degrees.

The eyewear further comprises a miniature processing unit 30 and an energizing unit 32. It is not shown specifically however should be appreciated that the processing unit is provided with appropriate memory and other peripheral circuitry.

In practice the processing unit is affixed to one of the lateral arms. Referring to FIG. 6b it is seen that processing unit 30 is affixed to the arm LA1 and that energizing unit 32 is affixed to the arm LA2.

It is not shown in details, but should be appreciated that signal exchange and communication is enabled between the video camera, the eye trackers, the display device and the processing unit by virtue of appropriate wiring or wirelessly It should be also appreciated that the energizing unit is electrically connected with the above components for energizing them.

Figure 8:
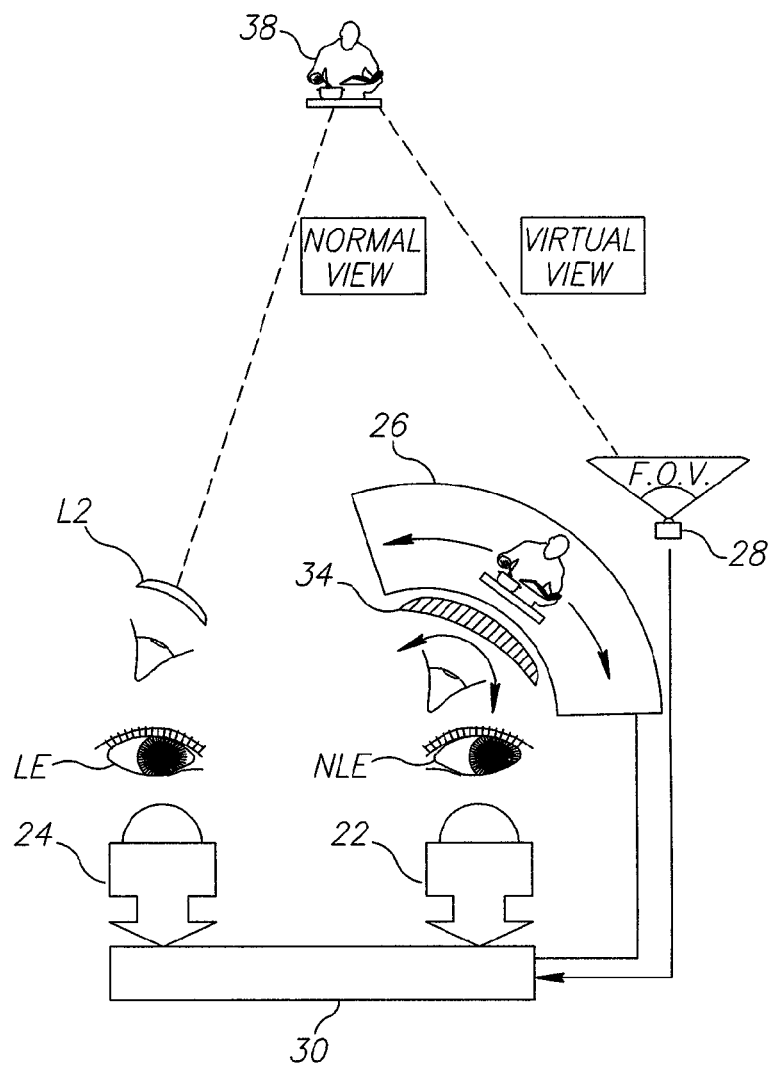
FIG. 8 shows an embodiment of the block diagram of the system of the present invention.

Furthermore one should bear in mind that in certain situation a single camera and a single display device would be sufficient. This is shown in FIGS. 6a, 6b and 8. In some other situations a plurality of cameras and a plurality of display devices would be required. This will be explained in details later on with reference to FIG. 9.

Referring again to FIG. 6b an eyepiece lens 34 is provided. This lens allows the non-leading eye NLE to focus on the display device 26 which is but a few centimeters from the non-leading eye. Instead of optical lens 34 a contact lens 36 put on the non-leading eye, as shown in FIG. 7, can be used for the same purpose.

Now with reference to FIGS. 8-9 the present invention will be explained in connection with some exemplary cases of visual impairment.

Case #1:

The case refers to a situation when a patient's left eye is the leading eye and patient's right eye is the non-leading eye. The non-leading eye still is able to perform some limited movements.

In FIG. 8 configuration of the system is shown as a block diagram. The block diagram suitable for this case includes those components which have been already mentioned above in connection with FIGS. 6a, 6b.

It is seen that lens L2 is located in front of leading eye LE. The lens L2 is a conventional lens. If the leading eye has no focusing problem, the diopter number prescribed for that lens can be zero. In all other cases, the diopter number of the leading eye lens L2 can be prescribed by optometrist.

Through this lens, the patient leading eye has an unobstructed view of the scene such that it can see for example an object 38 in front of it.

First eye tracker 24 is located in the lower portion of the leading eye lens L2 so as not to obscure the leading eye view (as much as practical) and at the same time to be capable to reliably track position of the leading eye. This is designated in FIG. 8 as normal view.

Wide angle display device 26 is located in front of the non-leading eye.

Eyepiece lens 34 is located between wide angle display device 26 and non-leading eye NLE so as to allow the non-leading eye to view the image of the object appearing on the display at a right focus. This eyepiece lens should have corrective diopter power required for the eye of the patient. So, the non-leading eye sees only virtual image of the object appearing on the display. This is designated in the FIG. 8 as virtual view.

Second eye tracker 22 is located in the lower portion of the non-leading eye display device 26 so as not to obscure the non-leading eye view and at the same time reliably track the non-leading eye position.

Wide angle digital video camera 28 is located at the right side of the non-leading eye so as to have unobstructed view of the external scene in front of the patient's head as it would be seen by a healthy non-leading eye. The camera can be provided with a suitable CCD or CMOS solid state sensor (or other kind of sensor) and have a lens with a field of view sufficient to cover the whole potential field of view that the non-leading eye NLE could have seen would it be capable to move normally. In practice this angle is confined within an angle of at least 70 degrees and preferably about 100 degrees.

Since the camera has a wide angle lens, it obtains instantaneously a large portion of the field of view that could be seen by a normal eye at the position of the non-leading eye. This position is critical since in order to perceive a three dimensional image, human brain has to receive simultaneously two slightly different images from both locations—the leading eye location and the non-leading eye location. The obtained image is then processed and manipulated by processing unit 30 in a fast way so as to properly track the rapid movements of the leading eye. It is schematically shown in FIG. 8 by an arrow showing that image seen by the camera is electronically sent from the camera to the processing unit. The other arrow shows that upon processing the shifted image is electronically sent to the display device.

As mentioned above it is preferable that the camera is capable to measure the distance to the object and has an autofocusing feature.

Case #2:

This case refers to a situation when patient's left eye is the leading eye and the right eye is the non-leading eye and the non-leading eye has full paralysis.

The block diagram of the system suitable for treatment of this case would be basically the same as seen in FIG. 8. However, in this case the second eye tracker would not be required since the non-leading eye is fully immobile due to paralysis and its direction is fixed with reference to the head's direction. Accordingly the gazing angle α of the non-leading eye is known in advance and it can be taken into consideration in all calculations necessary for correcting angular deviation between leading eye and non-leading eye.

Case #3:

This case addresses to a situation when both eyes of the patient gaze in abnormal directions (i.e. alternating strabismus, nystagmus etc.).

Figure 9:
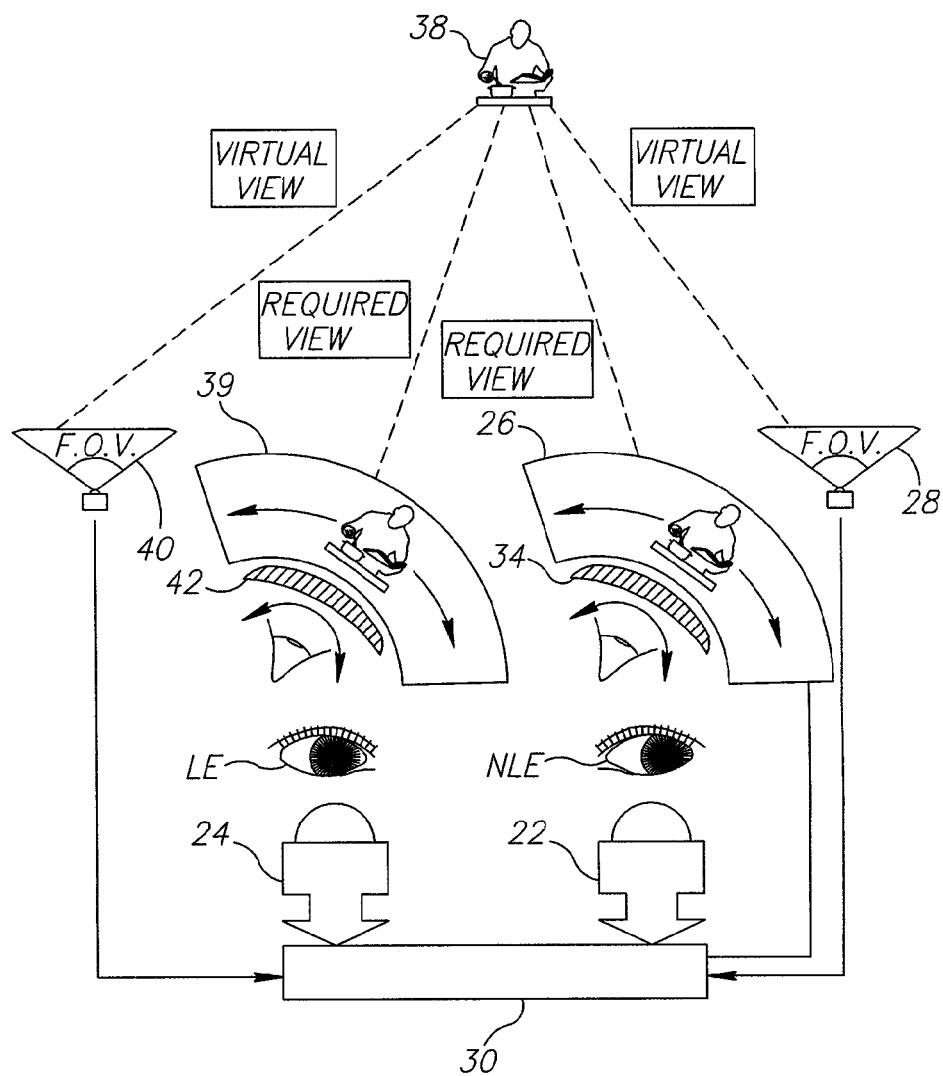
FIG. 9 shows an alternative embodiment of the block diagram of the system of the present invention.

The block diagram of the system is shown in FIG. 9. It can be easily seen that it is basically similar to the system presented on diagram seen in FIG. 8.

Accordingly the similar components are designated by similar reference numerals. However, configuration of the system suitable for treatment of this case would require an additional video camera 40 positioned near the leading eye and an additional wide angle display device 39 positioned in front of the leading eye.

An additional eyepiece lens 42 could be provided in front of the leading eye.

It is designated by straight lines the directions of virtual view between cameras and the object, as well as the directions of required view between the eyes and the object.

A non-limiting table below summarizes the possible hardware configurations of the system required for each of the above cases:

| Hardware Required | A healthy leading eye, a non-leading eye which has some moving capabilities (Case # 1) | A healthy leading eye, a non-leading eye fully paralysed (Case # 2) | Ocular misalignment in both eyes (case # 3) |
|---|---|---|---|
| Eye tracker in front of leading eye | 1 | 1 | 1 |
| Eye tracker in front of non-leading eye | 1 | 0 | 1 |
| Wide angle digital video camera near leading eye | 0 | 0 | 1 |
| Wide angle video camera near non-leading eye | 1 | 1 | 1 |
| Wide angle high definition display device near leading eye | 0 | 0 | 1 |
| Wide angle high definition display device near non-leading eye | 1 | 1 | 1 |

Now with reference to FIGS. 10-14 the method of treatment of visual impairment in accordance with the present invention will be explained in connection with the above mentioned three cases.

Case #1:

In the following calculations let's assume that the object is far away from the patient so both eyes should stare in parallel, in the exact same direction. The leading eye stares at an object in space.

Figure 10:
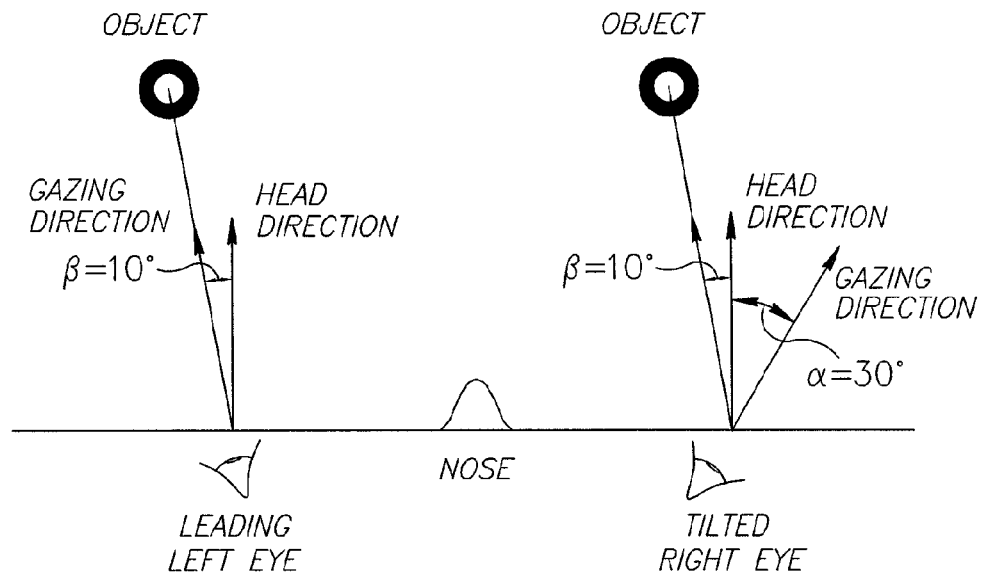
FIG. 10 shows schematically gazing direction and head direction of the leading eye and of the non-leading eye, before correction of angular deviation.

Let's assume that the object is located at an angle β-10° to the left (relative to head), as shown on the left side of FIG. 10. When the patient stares at the object the first eye tracker detects gazing direction of the leading eye, determines the staring angle β of the leading eye and sends this data to the processing unit.

A second eye tracker is positioned near the non-leading eye.

The non-leading eye stares at an arbitrary angle in space. Let's assume that the non-leading eye is gazing at an angle α=30° to the right, as shown on the right side of FIG. 10. This angle α might be caused by strabismus from which the patient suffers. The second eye tracker determines the staring angle α of the non-leading eye and sends this data to the processing unit.

Figure 11:
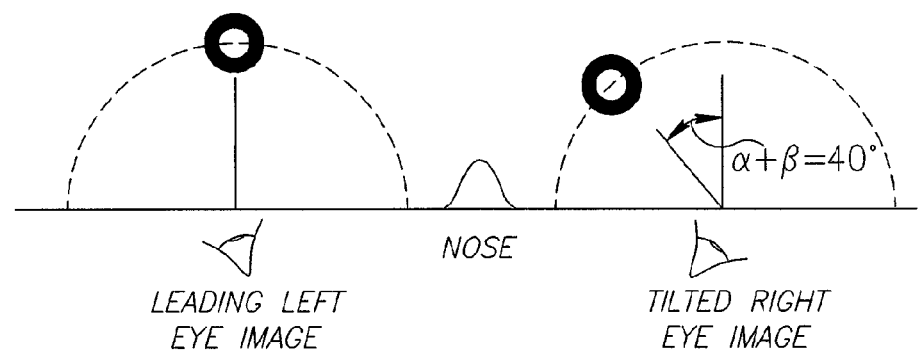
FIG. 11 shows schematically image perception of an object by the leading eye and by the non-leading eye, before correction of angular deviation.
Figure 12:
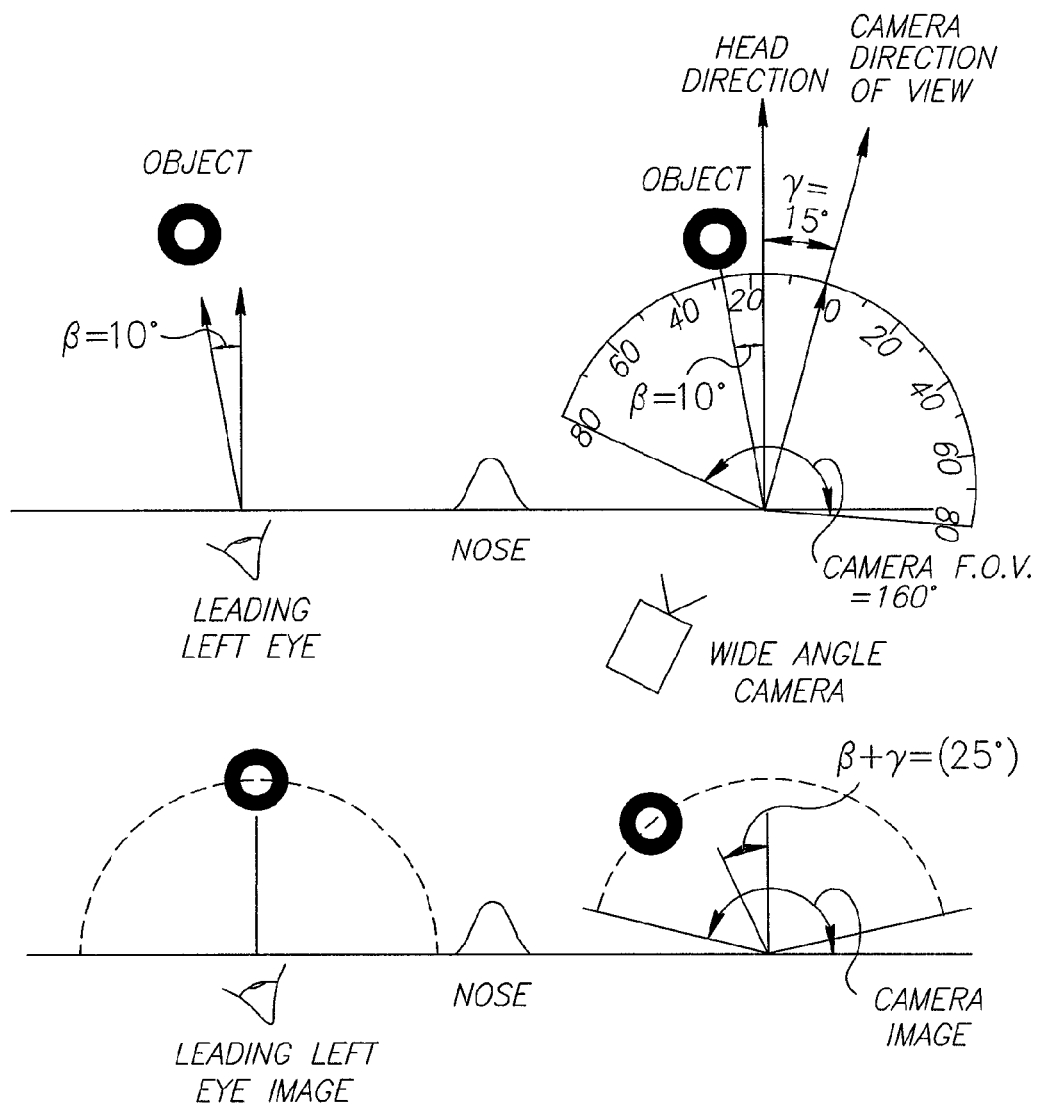
FIG. 12 shows schematically direction of view of the leading eye and camera direction of view, before correction of angular deviation.

Thus the leading eye sees the image of the object in the middle of its field of view while the non-leading eye could have seen the image of the object at an angle α+β=40° to the left of its gazing direction. This situation is shown in FIG. 11.

Such angular deviation brings to two different images which cannot be combined in the brain and the image which could have seen by the non-leading eye has to be suppressed to prevent diplopia. Let's assume that the video camera which captures image of the object is tilted to the right by an angle γ=15° relative to the head. This is shown at the right on FIG. 12. As a result of the tilting, the image of the object as "seen" by the video camera will be shifted at β+γ=25° to the left. This situation is shown on the right side of FIG. 12.

The image captured by the video camera is sent to the processing unit.

Using the image produced by the video camera, the processing unit calculates the distance of the object from the patient's eyes and stores this distance in its memory. The calculation can be performed by using a focusing techniques used in photography, e.g. those based on passive auto focusing, phase detection, contrast measurement, active auto focusing etc.

The wide angle display device is located in front of the non-leading eye and blocks the whole natural view from the non-leading eye. Let's also assume that the wide angle display device is permanently tilted to the right at an angle γ=15° so its center of display will be at the center of the potential 160° field of view of the non-leading eye. This is shown at the right side of FIG. 13.

Figure 13:
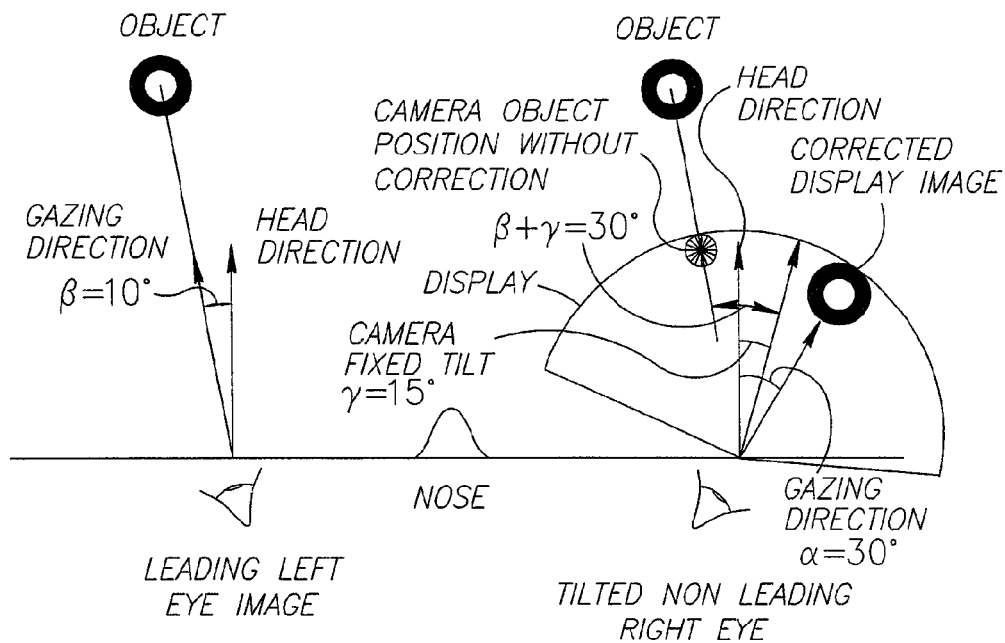
FIG. 13 shows schematically image perception of an object by the leading eye and by the non-leading eye, after correction of angular deviation.
Figure 13:
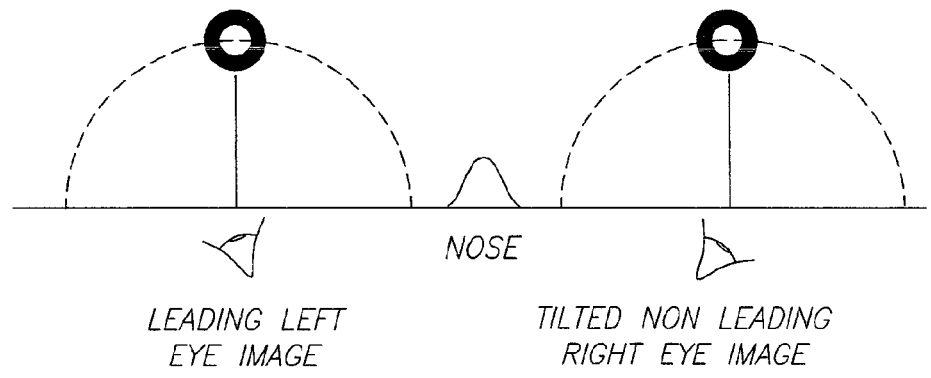

Processing unit 30 carries out the required image processing as mentioned above and calculates the required angle shift for shifting the image electronically in order to display the image precisely in front of the actual gazing direction of the non-leading eye. In our case the image has to be electronically shifted to the right by an angle equal to (β+γ)+(α−γ)−β+α−10+30−40°. After shifting the angular deviation in gazing directions of both eyes would be corrected and both eyes could see the image in the middle of the field of view, exactly in front of the gazing direction of their corresponding optical axes. This is shown in FIG. 13. Accordingly the patient's brain will be able to merge these two images into a single, normal stereoscopic image as though both eyes would stare at the object at the correct angle.

The image processing, calculating and correcting the angular deviation will be performed continuously by the system, such that the image projected in front of the non-leading eye all the time will be at the required direction depending on the direction that the leading eye is staring at.

Let's assume now that the object is not far away from the patient so both eyes should not stare in parallel at the object but rather at some convergence angle.

Figure 1:
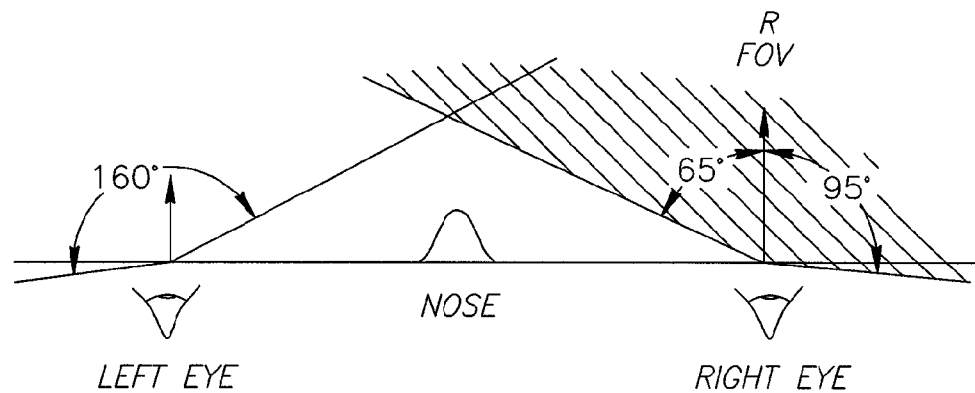
FIG. 1 shows schematically monocular field of view of normal eyes.
Figure 2:
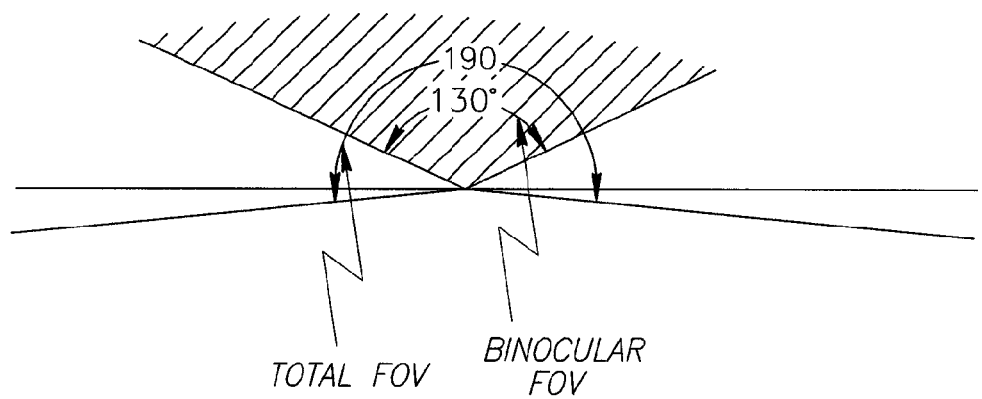
FIG. 2 shows schematically binocular field of view of normal eyes.
Figure 3:
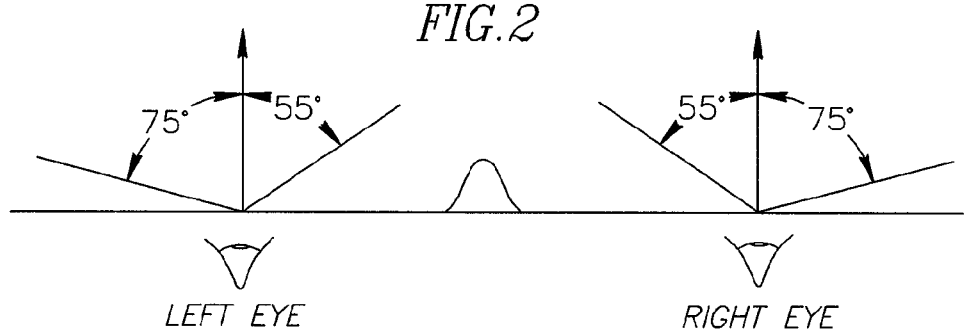
FIG. 3 shows schematically amplitudes of movements of normal eyes.
Figure 4:
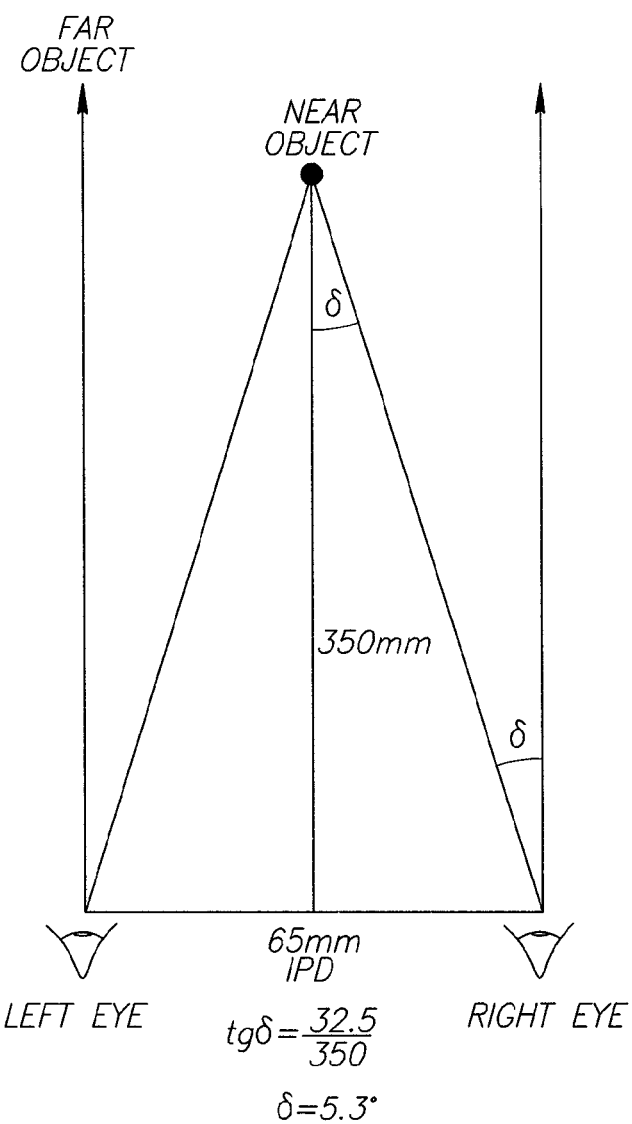
FIG. 4 shows schematically calculation of convergence angle

Let's assume for example, that the distance measuring feature measures the distance to the object be 350 mm. The processing unit calculates the convergences angle δ to be 5.3° as explained above and as shown in FIG. 4. Its easy to show that the total addition to the shift angle should be the δ angle.

So, in our case, if the object is 350 mm away from the patient, and as calculated above, the convergence angle δ=5.3°, the total angle that the image displayed in front of the non-leading eye has to be shifted to the left is α+δ=30+5.3=35.3°.

So also in this case, the non-leading eye would be perceiving the image projected in front of it on the display device as it were normal and staring at the object in the proper direction. This will allow the brain to perceive three dimensional image even though the non-leading eye is staring not at the object as it should have been.

In practice calculating the convergence angle is necessary when the distance between the object and the patient's head is, for example, less than 2 meters.

Figure 14:
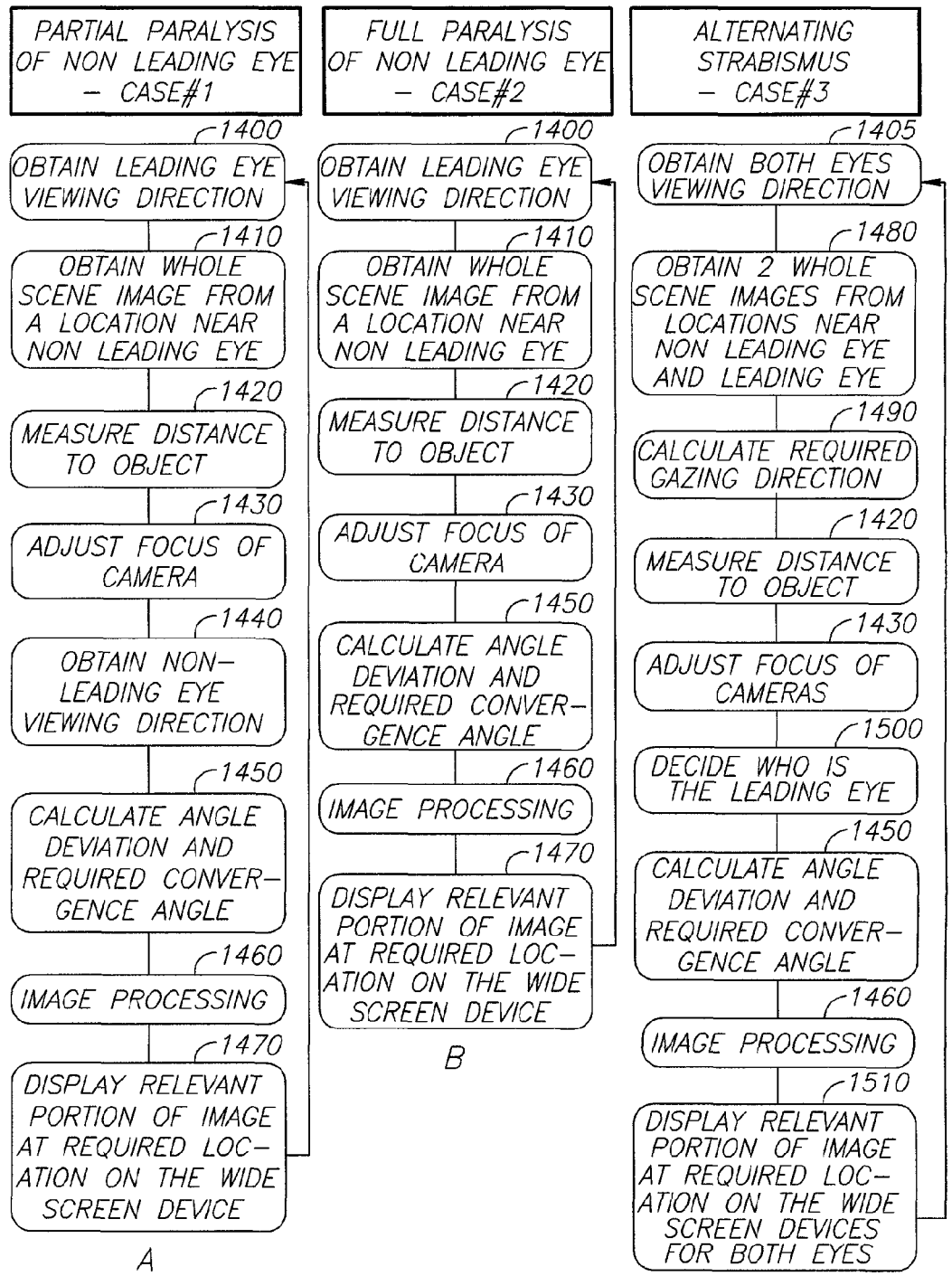
FIGS. 14a, b, c are flow chart diagrams of various embodiments of a method of the present invention.

Now with reference to FIG. 14 the process flow would be summarized in connection with all three cases.

In the first case the process steps are shown in FIG. 14a.

The treatment process begins from a step 1400, which is detecting gazing direction of the leading eye and obtaining staring angle. This is accomplished by eye tracker 24. The obtained staring angle is stored in the processing unit memory.

The next step is designated by numeral 1410 and it is obtaining whole image scene seen by the wide angle digital camera 28 having angle view which is sufficient for covering a major part of the scene.

At a next step, which is designated 1420, a distance to the viewed object is measured and the measured value is stored in the processing unit memory.

In a following step designated 1430 the camera focus is adjusted.

A further step which is designated 1440 comprises detecting gazing direction of the non-leading eye and obtaining its staring angle. This is accomplished by eye tracker 22

The obtained staring angle is stored in the processing unit memory.

At a next step designated 1450 a deviation between gazing angles of the leading eye and non-leading eye is calculated by the processing unit. Depending on the previously calculated distance to the object a convergence angle can be calculated as well.

At a next step designated 1460 the image produced by the camera is processed in such a manner that after the processing the image would be shifted to correct angular deviation of the non leading eye.

At a last step designated 1470 the shifted image is displayed on the wide angle display device 26 located in front of the non-leading eye.

The above sequence of steps is repeated continuously.

The process flow of the treatment method suitable for case 2 is shown in FIG. 14b.

One should bear in mind that the method suitable for case 1 would be basically similar for case 2 and accordingly similar process steps are designated in FIG. 14b by the similar reference numerals.

However in the method of treatment suitable for the case 2 the step 1440 is missing since gazing direction of the paralyzed non-leading eye is a priori known.

The process flow of method of treatment suitable for case 3 is shown in FIG. 14c.

Here again the similar steps are designated by similar reference numerals. However, in this case staring angle of both eyes should be determined according to some additional algorithm. According to one of such algorithms one eye is permanently defined by the processing unit as the leading eye and an average value of its staring angle is used in calculations instead of instantaneous values associated with the leading eye.

According to the other algorithms defining a leading eye can alternate automatically based on analysis of movements of both eyes.

The process flow for case 3 starts from step 1405, where gazing angles of both eyes are obtained. After this a step 1480 is carried out. The step 1480 comprises obtaining of two whole scene images with the aid of wide angle cameras 28, 36. The next step is designated 1490 and it comprises calculating required gazing direction. Still further steps 1420, 1430 are similar to the previous process flow referring to case 1. In a step 1500, based on collected data from both eyes, the leading eye is nominated. The next steps 1450, 1460 are similar to the process flow referring to case 1. The last step is designated 1510 and it comprises displaying of the shifted images on respecting wide angle display device located in front of each eye.

In this configuration, the patient will see a more stable image than the erratic image that he sees in real life without any correction of the angular deviations.

Thus by virtue of the system and method of the invention it is possible to treat visual impairment associated with diplopia-types and paralysis.

It is possible to treat the visual impairment by a compact system, which does not comprise mechanically moving components and this treatment can be accomplished with the aim of a convenient for the patient eyewear.

It should be appreciated that the present invention is not limited to the above-described examples and that one ordinarily skilled in the art can make changes and modifications without deviation from the scope of the invention, as will be defined in the appended claims.

So for example, external connection to the system can be provided instead of or in addition to the battery pack. This connection could be used for electric power input (for example for charging), data input and outputs such as calibration, history data, eye training exercises, virtual image insertion etc.

For higher resolutions, the wide angle digital camera can be equipped with plurality of image sensors.

Instead of wide angle display device affixed to a lens of the eyewear a retina scanning display or other technology can be used. An example of commercially available retinal scanning display one can mention retinal scanning display developed by the company Brother, Japan.

It should also be appreciated that the features disclosed in the foregoing description, and/or in the following claims, and/or in the accompanying drawings may, both separately and in any combination thereof, be material for realizing the present invention in diverse forms thereof.

When used in the following claims, the terms "comprise", "include", "have" and their conjugates mean "including but not limited to".

LIST OF REFERENCE NUMERALS

9 Patient
10 General view of the system
12 Head unit
14 Connecting cable
16 External processing and energizing unit
18 System configured as eyewear
20 Frame
22 Eye tracker
24 Eye tracker
26 Display device
28 Wide angle digital camera
30 Processing unit
32 Source of energy
34 Eye piece lens
36 Contact tense
38 Object
39 Display device
40 Wide angle digital camera
42 Eye piece lens
LE Leading eye
NLE Non-leading eye
1,2 Lens
LA1 Lateral arm
LA2 Lateral arm
1400, 1405 1410, 1420, 1430, 1440, 1450, 1460, 1470, 1480, 1490, 1500, 1510 Steps

The invention claimed is:

1. A method for treating of visual impairment associated with misalignment between eyes of a patient, said method comprising:
   selecting one eye as a leading eye while selecting a second eye as a non-leading eye,
   tracking a current position of the leading eye when it is staring at a scene and determining a current staring direction of the leading eye,
   obtaining electronically by an unmovable standstill digital video camera of an image of the scene stared at by the patient,
   tracking a current position of the non-leading eye and determining a staring direction of the non-leading eye,
   calculating an angular deviation between the staring direction of the leading eye and the staring direction of the non-leading eye,
   electronically processing the image of the scene such that upon processing the image becomes electronically shifted in accordance with the angular deviation and
   displaying a processed image in front of at least the non-leading eye.

2. The method of claim 1, comprising measuring a distance between the patient and the object.

3. The method of claim 2, comprising calculating a convergence angle between the staring direction of the leading eye and staring direction of the non-leading eye and correcting the angular deviation in accordance with the convergence angle.

4. The method of claim 1, in which the image is electronically obtained by a wide angle digital video camera having a view angle of at least 70 degrees.

5. The method of claim 1, comprising obtaining electronically of an image of the scene from a location near to the non-leading eye.

6. The method of claim 1, comprising electronically processing the image of the video camera such that it would be electronically shifted in accordance with the angular deviation and displaying the electronically shifted image in front of the non-leading eye.

7. The method of claim 4, comprising adjusting a focus of the camera.

8. A system for treating of visual impairment associated with misalignment between eyes of a patient, comprising:
   said system is dimensioned and configured as an eyewear with affixed thereto a tracking device capable of tracking movements of at least one of the patient's eyes,
   a substantially still, wide angle, digital image producing device capable of electronically producing an image of a scene which the patient is staring at, wherein the image producing device is secured on the eyewear such that there would be no relative displacement between the image producing device and the eyewear,
   a processing unit capable to electronically process the image, a display device capable of visually displaying the electronically processed image before the at least one of the patient's eyes and said eyewear is electrically connected with a source of energy for energizing the system.

9. The system of claim 8, in which said image producing device comprises a wide angle, high resolution, digital, video camera defined by an angle of view of at least 70 degrees.

10. The system of claim 8, in which said eyewear is configured as spectacles provided with a frame with a lens affixed thereto and said frame is provided with a first lateral arm and with a second lateral arm.

11. The system of claim 10, comprising a first eye tracking device and a second eye tracking device.

12. The system of claim 11 in which said camera is affixed to one of the lateral arms and said display device is affixed in front of at least one eye, the arrangement being such that the camera is proximate to the display device.

13. The system of claim 10 comprising a first camera affixed to the first lateral arm and a second camera affixed to the second lateral arm, a first display device located in front of one eye and a second display device located in front of the second eye.

14. The system of claim 8, in which said image producing device is provided with a distance measuring feature.

15. The system of claim 8, in which said camera is provided with an auto focusing feature.

\* \* \* \* \*